US008551066B2

(12) United States Patent
Wildeman et al.

(10) Patent No.: US 8,551,066 B2
(45) Date of Patent: Oct. 8, 2013

(54) ELASTOMERIC DIAPER FASTENING TAB

(75) Inventors: Martin Wildeman, Spartansburg, SC (US); Lori Shannon Sears, Taylors, SC (US)

(73) Assignee: Tietex International Ltd., Spartanburg, SC (US)

( * ) Notice: Subject to any disclaimer, the term of this patent is extended or adjusted under 35 U.S.C. 154(b) by 277 days.

(21) Appl. No.: 12/970,621

(22) Filed: Dec. 16, 2010

(65) Prior Publication Data

US 2011/0152819 A1 Jun. 23, 2011

Related U.S. Application Data

(60) Provisional application No. 61/287,928, filed on Dec. 18, 2009.

(51) Int. Cl.
*A61F 13/15* (2006.01)
(52) U.S. Cl.
USPC ............................................. 604/391
(58) Field of Classification Search
USPC ............... 604/385.27, 391; 442/402; 428/37; 66/192, 193
See application file for complete search history.

(56) References Cited

U.S. PATENT DOCUMENTS

| | | | |
|---|---|---|---|
| 3,664,336 A | 5/1972 | Gelston | |
| 4,052,866 A * | 10/1977 | Saunders | 66/193 |
| 4,861,652 A | 8/1989 | Lippert | |
| 4,931,343 A | 6/1990 | Becker et al. | |
| 5,368,668 A * | 11/1994 | Tochacek et al. | 156/93 |
| 5,916,207 A | 6/1999 | Toyoda et al. | |
| 6,419,667 B1 | 7/2002 | Avalon et al. | |
| 6,855,392 B2 | 2/2005 | Wildeman et al. | |
| 6,869,660 B2 | 3/2005 | Wildeman | |
| 7,294,387 B2 | 11/2007 | Wildeman | |
| 2003/0056703 A1 | 3/2003 | Blake | |
| 2003/0077970 A1 | 4/2003 | Delucia et al. | |
| 2003/0109844 A1 * | 6/2003 | Gibbs | 604/389 |
| 2008/0280094 A1 | 11/2008 | Wildeman et al. | |

OTHER PUBLICATIONS

PCT International Search Report and Written Opinion for Corresponding International Application No. PCT/US 10/03201.

* cited by examiner

*Primary Examiner* — Jackie Ho
*Assistant Examiner* — Peter S Vasat
(74) *Attorney, Agent, or Firm* — Maynard, Cooper & Gale, PC (57) ABSTRACT

A diaper fastening system including at least one elastomeric connection tab disposed at a side portion of the diaper. The connection tab has a body portion of stitch-bonded construction including an elastomeric expansion zone. The elastomeric expansion zone includes an inelastic stitching substrate of fibrous material with a plurality of accordion pleats and a zigzag network of elastomeric yarns disposed in underlying relation to the pleats. The zigzag network is adapted to apply contracting forces to the stitching substrate in the length dimension of the connection tab.

20 Claims, 6 Drawing Sheets

ELASTOMERIC DIAPER FASTENING TAB

CROSS-REFERENCE TO RELATED APPLICATIONS

This non-provisional application claims the benefit of, and priority from, U.S. provisional application 61/287,928 filed Dec. 18, 2009, the contents of which are hereby incorporated by reference in their entirety as if set forth fully herein.

TECHNICAL FIELD

The present invention relates generally to stretchable fastening tabs for tear-away attachment systems, and more particularly, to diaper closure systems incorporating stretchable fastening tabs as well as other environments of use where stretchable fastening tabs may be useful.

BACKGROUND OF THE INVENTION

In recent years snug fit has been a focus for diaper manufacturers seeking to improve the containment of urinary and bowel release. In accordance with this effort, stretchable attachment tabs are used as part of the closure system. During a fastening operation, the tab can be stretched as it is pulled into place across a wearer's abdomen to engage and lock onto a complementary attachment landing zone. In the fastened condition the stretched tab provides a snug fit while still permitting a degree of expansion and contraction to promote comfort.

According to one prior known practice, stretch features in diaper components have been achieved by gluing cut strands of an elastomeric yarn such as SPANDEX® or the like in sandwiched relation between layers of nonwoven fabric. According to another practice, a stretchable polymeric film is sandwiched between layers of nonwoven fabric. While such techniques may provide a level of benefit, they nonetheless require a substantial percentage of elastomeric material and the formation techniques are relatively complex.

SUMMARY OF THE INVENTION

The present invention provides advantages and alternatives over the prior art by providing a diaper fastening tab incorporating a stretchable textile material of stitch-bonded construction. The textile incorporates a fibrous stitching substrate formed from one or more layers of non-woven material. Stitch patterns forming ladder segments of elastomeric yarns stitched in crossing relation between anchoring linear stitch lines of substantially inelastic yarns extend in parallel relation to one another in the machine direction of the fabric.

In accordance with one exemplary feature, a diaper fastening tab may be provided having an expansion zone formed from a plurality of individual stitched-in ladder segments. The ladder segments may include pairs of opposing complementary linear stitch lines formed from substantially inelastic yarns running in the machine direction through a fibrous stitching substrate. The complementary linear stitch lines are spaced apart from one another with a number of unthreaded stitching needles removed between the linear stitch lines. Within each ladder segment, an elastomeric yarn is stitched through the fibrous substrate in a switch-back arrangement running between the complementary linear stitch lines such that segments of the elastomeric yarn are oriented transverse to the machine direction. Contraction forces imparted by the elastomeric yarn pull the complementary linear stitch lines towards one another such that the fibrous substrate is formed into expansible accordion pleats corresponding to the stitched-in ladder segments.

In accordance with one exemplary practice, a diaper fastening tab may be provided incorporating an expansion zone having multiple stitched-in ladder segments which each include one or more elastomeric yarns stitched through a fibrous substrate in a switch-back arrangement between opposing complementary linear stitch lines. The stitched-in ladder segments may be arranged in contiguous groups such that adjacent ladder segments within the groups share a common linear stitch line.

In accordance with another potentially preferred practice, a diaper fastening tab may be provided incorporating an expansion zone having multiple contiguous groups of stitched-in ladder segments arranged in adjacent, spaced-apart relation with unstitched zones between adjacent groups to define a discontinuous expansion zone providing controlled stretch in the length dimension of the fastening tab in combination with limited contraction in the width dimension and low curling. Each of the ladder segments within the contiguous groups may include one or more elastomeric yarns stitched through a fibrous substrate in a switch-back arrangement between opposing complementary linear stitch lines.

In accordance with one exemplary aspect, the present invention provides a diaper fastening system including a landing zone disposed across a portion of the diaper adapted for positioning in overlying relating to a wearer's abdomen. The landing zone has a surface at least partially covered with a material defining a first half of a hook and loop connection system. The diaper fastening system also includes at least one elastomeric connection tab disposed at a side portion of the diaper. The connection tab has a body portion of stitch-bonded construction including a free end projecting away from the diaper. The free end includes a base operatively connected to a material forming a second half of the hook and loop connection system. The body portion includes an elastomeric expansion zone. The elastomeric expansion zone includes an inelastic stitching substrate of fibrous material. The elastomeric expansion zone includes a plurality of accordion pleats of the stitching substrate with a zigzag network of elastomeric yarns disposed in underlying relation to the pleats. The zigzag network is adapted to apply contracting forces to the stitching substrate in the length dimension of the connection tab. The accordion pleats are formed by corresponding stitched-in ladder segments including an elastomeric yarn stitched in tension through the stitching substrate in switch-back relation between opposing linear stitch lines of inelastic yarns stitched through the stitching substrate. The linear stitch lines are oriented transverse to the direction of stretch. The elastomeric expansion zone is stretchable in the length dimension of the connection tab to at least 150% of its initial length without failure.

In accordance with another exemplary aspect, the present invention provides a diaper fastening system including a landing zone disposed across a portion of the diaper adapted for positioning in overlying relating to a wearer's abdomen. The landing zone has a surface at least partially covered with a material defining a first half of a hook and loop connection system. The diaper fastening system also includes at least one elastomeric connection tab disposed at a side portion of the diaper. The connection tab has a body portion of stitch-bonded construction including a free end projecting away from the diaper. The free end includes a base operatively connected to a material forming a second half of the hook and loop connection system. The body portion includes an elastomeric expansion zone. The elastomeric expansion zone includes an inelastic stitching substrate of fibrous material. The elastomeric expansion zone includes a plurality of accordion pleats of the stitching substrate with a zigzag network of elastomeric yarns disposed in underlying relation to the pleats. The zigzag network is adapted to apply contracting forces to the stitching substrate in the length dimension of the connection tab. The accordion pleats are formed by corresponding stitched-in ladder segments including an elastomeric yarn stitched in tension through the stitching substrate in switch-back relation between opposing linear stitch lines of inelastic yarns stitched through the stitching substrate. The linear stitch lines are oriented transverse to the direction of stretch. A portion of the stitching substrate extends away from the expansion zone and defines the base operatively connected to the material forming the second half of the hook and loop connection. The elastomeric expansion zone includes a first group of accordion pleats and at least a second group of accordion pleats separated by an inelastic spacing segment which extends in substantially spanning relation across the entire width of the elastomeric connection tab. The elastomeric expansion zone is stretchable in the length dimension of the connection tab to at least 150% of its initial length without failure.

In accordance with still another exemplary aspect, the present invention provides a diaper fastening system including a landing zone disposed across a portion of the diaper adapted for positioning in overlying relating to a wearer's abdomen. The landing zone has a surface at least partially covered with a material defining a first half of a hook and loop connection system. The diaper fastening system also includes at least one elastomeric connection tab disposed at a side portion of the diaper. The connection tab has a unitary body portion of stitch-bonded construction including a free end projecting away from the diaper. The free end includes a base operatively connected to a material forming a second half of the hook and loop connection system. The body portion includes an elastomeric expansion zone. The elastomeric expansion zone includes an inelastic stitching substrate of fibrous material. The elastomeric expansion zone includes a plurality of accordion pleats of the stitching substrate with a zigzag network of elastomeric yarns disposed in underlying relation to the pleats. The zigzag network is adapted to apply contracting forces to the stitching substrate in the length dimension of the connection tab. The accordion pleats are formed by corresponding stitched-in ladder segments including an elastomeric yarn stitched in tension through the stitching substrate in switch-back relation between opposing linear stitch lines of inelastic yarns stitched through the stitching substrate. The linear stitch lines are oriented transverse to the direction of stretch. A portion of the stitching substrate extends away from the expansion zone and defines the base operatively connected to the material forming the second half of the hook and loop connection. At least a first one of the ladder segments is oriented in side-by-side contacting relation with at least a second one of the ladder segments to define a contiguous group disposed across a portion of the expansion zone with a common linear stitch line is shared by adjacent ladder segments within the contiguous group. Two or more of such contiguous groups are disposed in spaced-apart relation within the elastomeric expansion zone with inelastic spacing segments of the stitching substrate disposed between adjacent contiguous groups. The inelastic spacing segments may extend substantially between upper lower edges of the elastomeric connection tab. The elastomeric expansion zone is stretchable in the length dimension of the connection tab by at least 50% without failure. The expansion zone recovers to within 15% of its initial length upon removal of tensioning force following a 50% extension in the length dimension. A 50% extension of the expansion zone in the length dimension of the connection tab is accompanied by not more than about a 20% reduction in the width dimension of the connection tab transverse to the direction of stretch.

BRIEF DESCRIPTION OF THE DRAWINGS

The accompanying drawings which are incorporated in and which constitute a part of this specification illustrate several exemplary constructions and procedures in accordance with the present invention and, together with the general description of the invention given above and the detailed description set forth below, serve to explain the principles of the invention wherein.

While the invention has been illustrated and will hereinafter be described in connection with certain exemplary embodiments and practices, it is to be understood that in no event is the invention to be limited to such illustrated and described embodiments and practices. On the contrary, it is intended that the present invention shall extend to all alternatives and modifications as may embrace the general principles of this invention within the full and true spirit and scope thereof.

DESCRIPTION OF THE PREFERRED EMBODIMENTS

Figure 1:
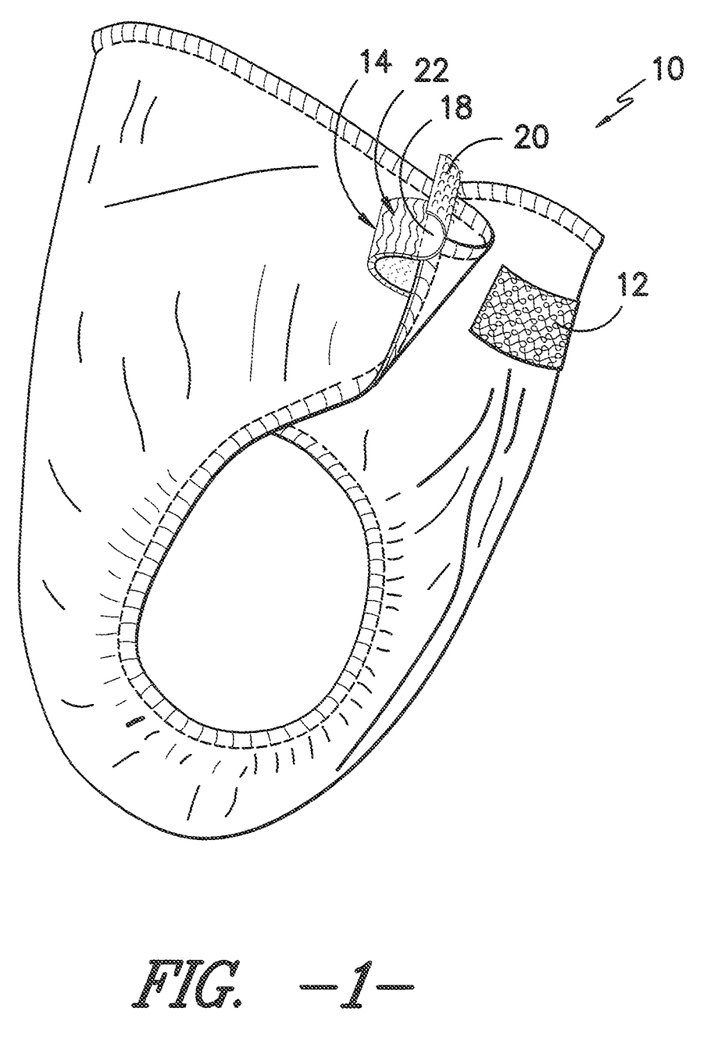
FIG. 1 illustrates an exemplary diaper incorporating an attachment tab formed from a portion of the exemplary stitch-bonded fabric.

Reference will now be made to the drawings wherein, to the extent possible, like reference numerals designate like elements in the various views. In FIG. 1, there is illustrated a diaper 10 including a releasable, adjustable fastening assembly. The exemplary fastening assembly includes a landing zone 12 of a material segment disposed across a portion of the diaper 10 generally overlying a wearer's upper abdominal region. By way of example only, the landing zone 12 may be formed from a loop fabric defining one half of a hook and loop connection system as will be well known to those of skill in the art.

In the illustrated exemplary arrangement, the fastening assembly further includes a stretchable tab member 14 which may be formed from a segment of stitch-bonded fabric of stretchable character as will be described further hereinafter. In this regard, it is to be understood that while only one side of the diaper 10 is shown, a stretchable tab member 14 may be positioned on each side to facilitate closing if desired. As best seen through joint reference to FIGS. 1 and 2, in the exemplary embodiment the stretchable tab member 14 includes a body portion having a proximal end 16 (FIG. 2) which may be secured to a side panel of the diaper 10 by lamination, adhesive bonding, stitching or other joining techniques as will be known to those of skill in the art. The body portion also includes an outwardly projecting distal end 18 which may be grasped by a person fitting the diaper to the wearer.

Figure 2:
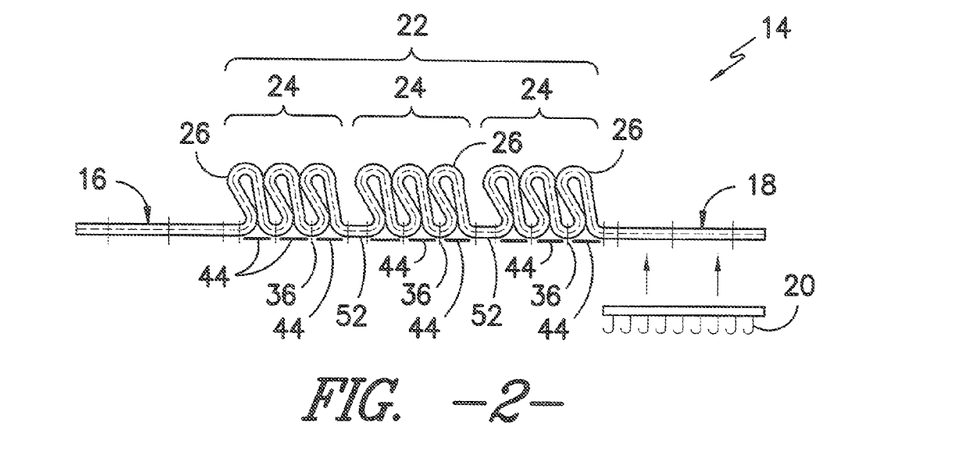
FIG. 2 is a schematic, partial assembly view illustrating operative connection of a hook tab material across a surface at the distal end of the attachment tab of FIG. 1.

As shown, the distal end 18 of the body portion may support an attachment surface formed from a segment of hook fabric 20 which may be secured across a face of the distal end 18 by lamination, adhesive bonding, stitching or other joining techniques as will be known to those of skill in the art. In this regard, the term "hook fabric" is meant to include any structure having a plurality of outwardly projecting hooking elements having a geometry adapted to engage the surface of the landing zone in a tear-away connection. By way of example only, and not limitation, such hooking elements may have a hooked terminal end and/or an enlarged terminal end such as a mushroom shape or the like adapted to become engaged within a loop fabric forming the landing zone 12. Of course, it is to be appreciated that the relative positions of loop fabric and hook fabric may be reversed if desired such that the hook fabric 20 is disposed at the landing zone 12 to engage loop fabric on the stretchable tab member 14.

In the exemplary tab member 14, the body portion includes an expansion zone 22 oriented between the proximal end 16 and the distal end 18. As best seen in FIG. 2, the expansion zone 22 may be made up of an array of sub-zones 24, which each include one or more expansible accordion pleats 26 formed by the contraction of elastomeric stitching yarns stitched in a switchback pattern through a fibrous substrate between linear stitch lines as will be described further hereinafter through reference to exemplary practices. In this regard, while the expansion zone 22 in the exemplary tab member 14 illustrated in FIG. 2 includes three sub-zones 24 arranged with intermediate spacing segments 52 between the sub-zones, it is likewise contemplated that a greater or lesser number of sub-zones 24 may be utilized. It is also contemplated that each sub-zone 24 may contain a larger or smaller number of pleats 26 and that different sub-zones 24 may contain differing numbers of pleats 26. It is also contemplated that intermediate spacing segments 52 may be eliminated if desired such that the expansion zone 22 is of substantially continuous character.

Regardless of the particular configuration of the expansion zone 22 in the tab member 14, the person applying the diaper 10 to the wearer may grasp the outwardly projecting distal end 18 and pull it towards the landing zone 12 to make the desired connection. During this application process, the tab member 14 is stretched to an elongated, tensioned condition by a flattening out of the accordion pleats. In this regard, the expansion zone may be stretchable in the length dimension of the tab member to at least 150% of its initial length (i.e. 50% stretch) without failure and more preferably will be stretchable in the length dimension of the tab member to at least 200% of its initial length without failure. The expansion zone will preferably recover to within 15% of its original length upon removal of tensioning force. The expansion zone 22 is preferably characterized by an elastic modulus in the length dimension such that a segment of the expansion zone having an untensioned width of 25 mm and length of 70 mm may be reversibly stretched to a length between about 91 mm (30% stretch) and about 133 mm (90% stretch) upon the application of 1000 grams force and may be reversibly stretched to a length between about 98 mm (40% stretch) and about 175 mm (150% stretch) upon the application of 1500 grams force. Thus, the elastic modulus of the overall expansion zone 22 is preferably at least about 40 to 150 grams force per centimeter width per 10% stretch and more preferably at least about 50 to 80 grams force per centimeter width per 10% stretch. However, this level may be higher or lower if desired. The material forming the expansion zone 22 thus provides a relatively strong elastic recovery force. Upon engagement between the tab member 14 and the landing zone 12, the tab member 14 is held in the elongated, tensioned condition with the internal stretch recovery force of the elastomeric stitching yarns in the tab member 14 urging the tab member to recover its tension-free pleated state. In this condition, the tab member 14 may extend and contract as the user moves. However, the internal tension urges the tab member 14 continuously back towards its shortened state. Thus, a snug fit is maintained continuously throughout use.

Figure 3:
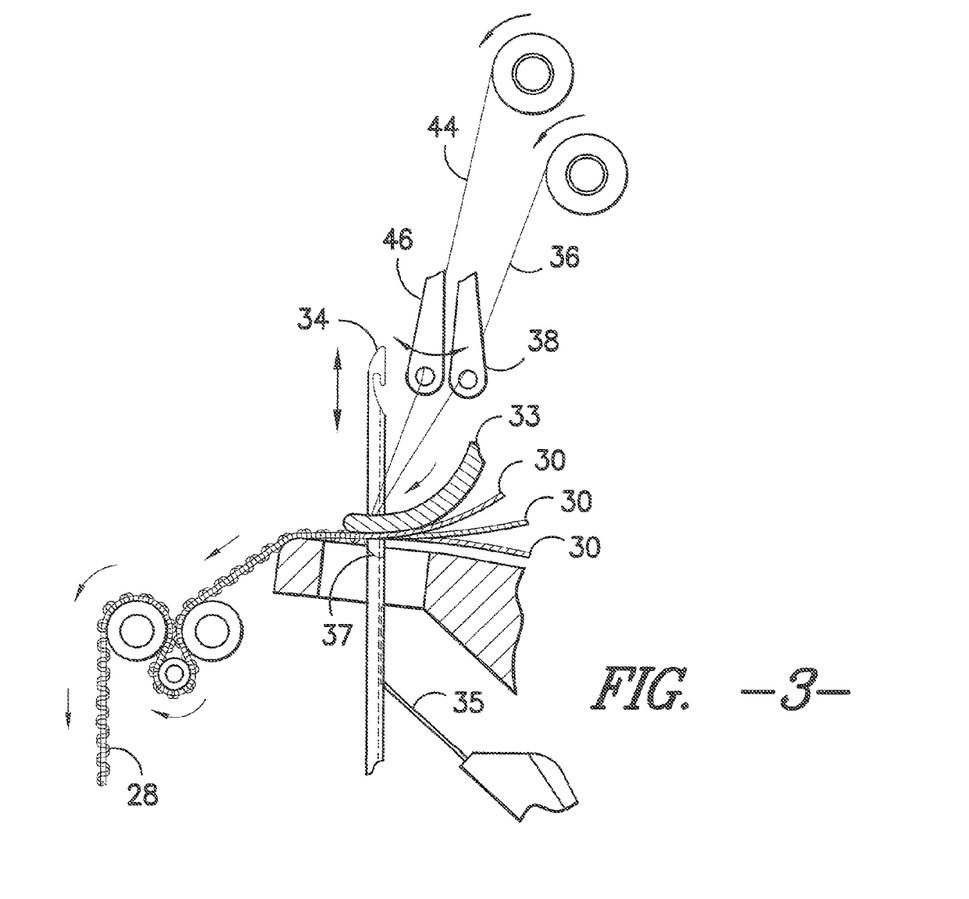
FIG. 3 illustrates schematically a two bar stitch-bonding process for stitching a pattern of elastic and inelastic yarns through a multi-layer substrate to form segments of the attachment tab of FIG. 1.
Figure 7:
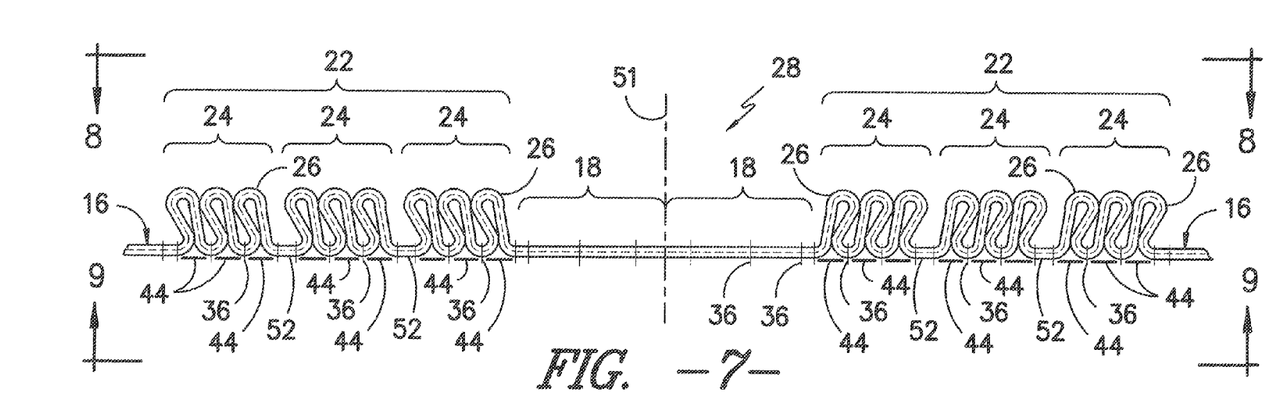
FIG. 7 is a schematic cross-sectional view of an exemplary stitch-bonded fabric with expansible stretch zones made up from groups of accordion pleats formed by the ladder segments of FIG. 6 to provide elastomeric character to the formed fabric.

Referring jointly to FIGS. 1, 3 and 7, the body portion of the stretchable tab member 14 may be cut as a unitary piece from a stretchable fabric 28 shown schematically in FIGS. 3 and 7 which is formed using stitch-bonding (also referred to as stitch knitting) techniques. In such a process, stitching yarns are passed in stitching relation through a substrate formed from one or more layers of material so as to form a coordinated arrangement of surface stitches. Such a process is described generally in U.S. Pat. No. 6,855,392 to Wildeman et al. which is incorporated herein by reference.

By way of example only, one method contemplated for formation of a stretchable fabric for use in the body portion of the tab member 14 involves a so called two bar stitch-bonding procedure shown schematically in FIG. 3. In the illustrated exemplary practice, multiple plies of a substrate material 30 of fibrous nonwoven construction such as a spun bonded fleece, or carded thermobond web formed from materials such as polyester, polypropylene or blends thereof may be conveyed to a stitch-forming position in the direction indicated by the arrows. Combinations of materials may also be used. The plies of substrate material 30 may be either similar or dissimilar to one another in construction and/or composition. In this regard, while the exemplary process is illustrated as incorporating three layers of substrate material 30, it will be understood that a greater or lesser number of layers may likewise be utilized. In the event that multiple plies of substrate material 30 are used, such multiple plies cooperatively form the substrate structure. The total mass per unit area of the substrate structure is preferably in the range of about 15 to 150 grams per square meter although higher or lower weights may be used if desired.

By way of example only, and not limitation, in one exemplary construction each ply of substrate material 30 may be a spun bonded polypropylene fleece having a mass per unit area of about 5 to 50 grams per square meter and more preferably about 15 grams per square meter. Such material is preferably present with 1 to about 6 layers and most preferably about 3 layers, although a greater number of layers may be used if desired. In another exemplary construction, each ply may be a carded thermobond web of polypropylene fiber having a mass per unit area of about 10 to 80 grams per square meter and more preferably about 20 grams per square meter. Such material is preferably present with 1 to about 6 layers and most preferably about 3 layers, although a greater number of layers may be used if desired.

In accordance with one potentially desirable construction, multiple layers of carded thermobond polypropylene web material as described may be plied together with one or more layers of spunbonded polypropylene fleece as described to form a multi-layer substrate. In this regard, the carded thermobond web may have a fiber orientation aligned substantially in the machine direction (i.e. the direction of web travel) thereby increasing strength in the machine direction. The presence of the spunbonded fleece enhances strength in the cross-machine direction. A benefit of having increased strength in the machine direction may be a reduced propensity for contraction of the tab member 14 in the width dimension (corresponding to the machine direction) upon stretching in the length dimension (corresponding to the cross-machine direction) thereby enhancing dimensional stability.

The stitching substrate typically is substantially inelastic without substantial inherent stretch and recovery character. In this regard, such materials can typically be stretched by no more than about 20% in any direction without experiencing either (i) failure or (ii) a permanent distortion of at least 5% following release of the stretching force. More typically, such preferred materials can be stretched by no more than about 15% in any direction without experiencing either (i) failure or (ii) a permanent distortion of at least 5% following release of the stretching force.

As indicated, the stitching substrate may be formed from a single ply of material if desired. However, the use of multiple plies is believed to provide increased strength and resistance to stretch for a given overall weight and may aid in reducing curl in the finished stitch bonded product. The elimination of such curl may facilitate subsequent cutting operation in which stretch tabs as described previously are segmented from the formed stitch-bonded material. The substrate material 30 may be delivered without significant underfeed or overfeed. However, delivery rates may be adjusted as desired.

As illustrated, the stitch bonding machine typically incorporates a row of reciprocating needles 34 (only one shown) extending in adjacent relation to one another across the width of the substrate material 30 substantially transverse to the direction of movement of the substrate material 30. So called "sinker fingers" 33 (also known as nebs) may extend from a sinker bar for disposition between the needles to aid in pressing the plies of substrate material together and to hold segments of stitching yarns which cross between needles in slightly raised relation from the substrate material 30. The sinker fingers 33 may also be eliminated if desired. By way of example only, and not limitation, the sinker fingers 33 may have a height of about 0.5 mm to 4 mm and most preferably about 1 mm although other sizes may likewise be used.

Figure 4:
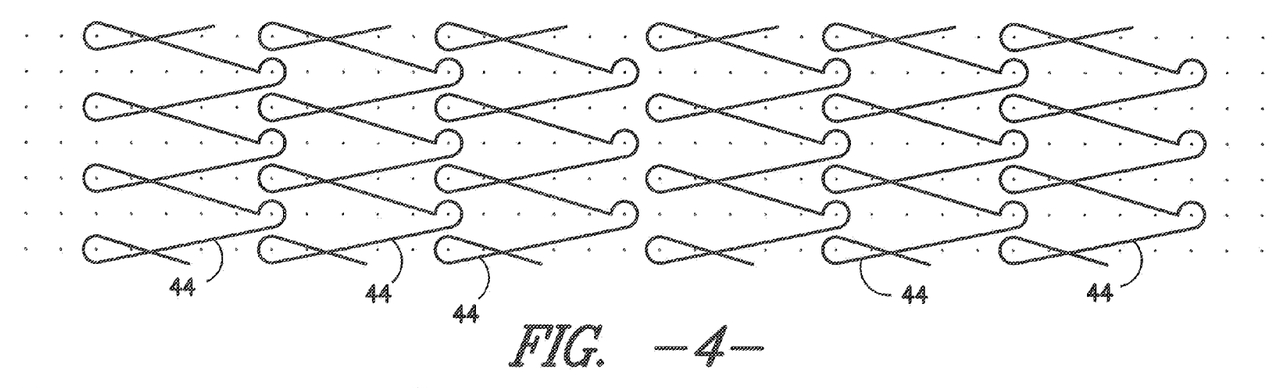
FIG. 4 is a needle point diagram illustrating an exemplary stitch pattern for elastomeric yarns formed by a first bar in the stitch-bonding process of FIG. 3 to provide elastomeric character to the attachment tab of FIG. 1.
Figure 5:
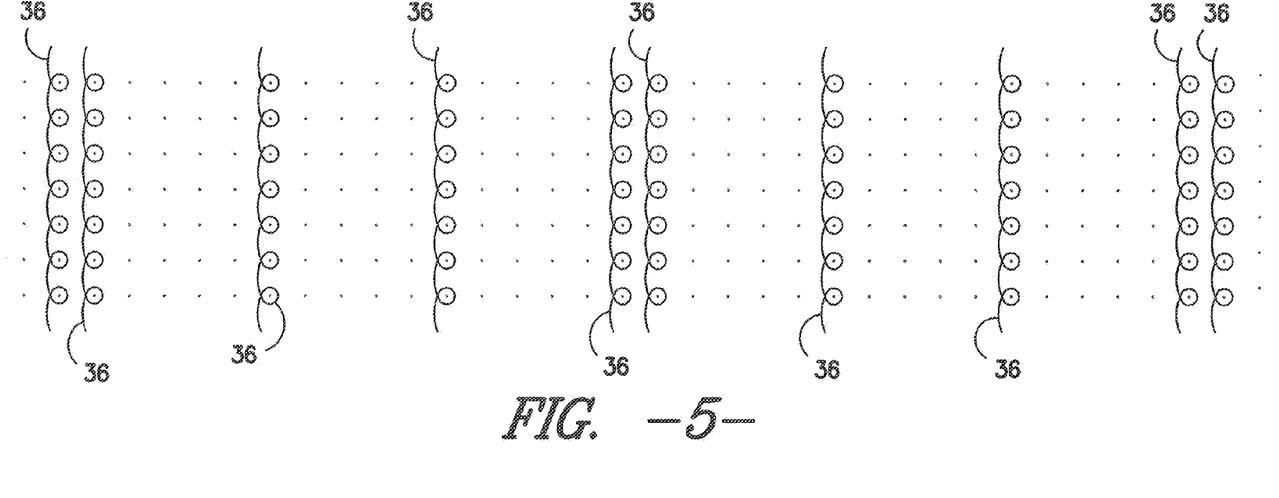
FIG. 5 is a needle point diagram illustrating an exemplary stitch pattern for inelastic yarns defining linear stitch lines formed by a second bar in the stitch-bonding process of FIG. 3 to define boundaries for the elastomeric yarns of FIG. 4.

Referring jointly to FIGS. 3-5, according to the illustrated exemplary practice, two yarn systems (i.e. two bars) are used to form stitches through the substrate material 30. A first group of substantially inelastic yarns 36 of low stretchability such as a commodity polyester yarn having a linear density of about 40 to about 400 denier is carried by a first guide 38 for cooperative engagement with predefined groups of the needles 34. By way of example only, and not limitation, one exemplary inelastic yarn 36 is a 150 denier, 34 filament textured polyester. Of course, higher or lower denier levels may be used if desired.

A second group of elastomeric yarns 44 of high stretchability such as SPANDEX®, HYTREL® or the like, having a linear density of about 40 to about 1,000 denier is carried by a second guide 46 for cooperative engagement with other groups of needles 34. In this regard, the term "elastomeric yarn" is defined as a yarn which is stretchable to at least twice its original length by the application of tension followed by a return to its original length under ambient conditions upon the removal of the tensioning force. Inelastic yarns do not satisfy this criterion. By way of example only, and not limitation, one exemplary elastomeric yarn 44 is a 560 denier SPANDEX® yarn having a 70 denier 34 filament cover with 15 turns. Of course, higher or lower denier levels may be used if desired.

As will be appreciated by those of skill in the art, during the stitch-bonding process a needle 34 (shown in greatly exaggerated dimension) pierces the substrate material 30 and engages stitching yarns delivered into position by the yarn guides such that the stitching yarns are captured within a hook portion of the needle 34. As the needle is reciprocated downwardly, a closing element 35 such as a closing wire which moves relative to the needle 34 closes the hook portion to hold the stitching yarns therein. With the hook portion closed, the captured stitching yarns are pulled through the interior of an immediately preceding yarn loop 37 disposed around the shank of the needle 34 at a position below the substrate material 30. As the captured stitching yarns are pulled through the interior of the preceding yarn loop 37 a stitch is formed which is knocked off of the needle 34. As the needle 34 is raised back through the substrate material 30, the hook portion is reopened and a new yarn loop 37 moves out of the hook portion and is held around the shank of the needle 34 for acceptance of captured yarns and formation of a subsequent stitch during the next down stroke. During this process individual stitching yarns may be held at a single needle 34 or may be shifted back and forth laterally between needles.

The so called gauge or needle density in the cross machine direction maybe adjusted as desired. By way of example only, and not limitation, it is contemplated that the gauge may be in the range of about 7 to 28 needles per inch and will more preferably be about 12 to 16 and will most preferably be about 14 needles per inch, although higher and lower needle densities may likewise be used if desired. Needles which are not used are preferably removed. By way of example only, and not limitation, the stitch bonding machine may be set to apply stitches in the machine direction at a level of about 4 to about 20 stitches per inch (also referred to as courses per inch or CPI) and will more preferably apply stitches in the machine direction at a level of about 8 to about 16 CPI and will most preferably apply stitches in the machine direction at a level of about 12 CPI although higher and lower stitch densities may likewise be used if desired.

Figure 6:
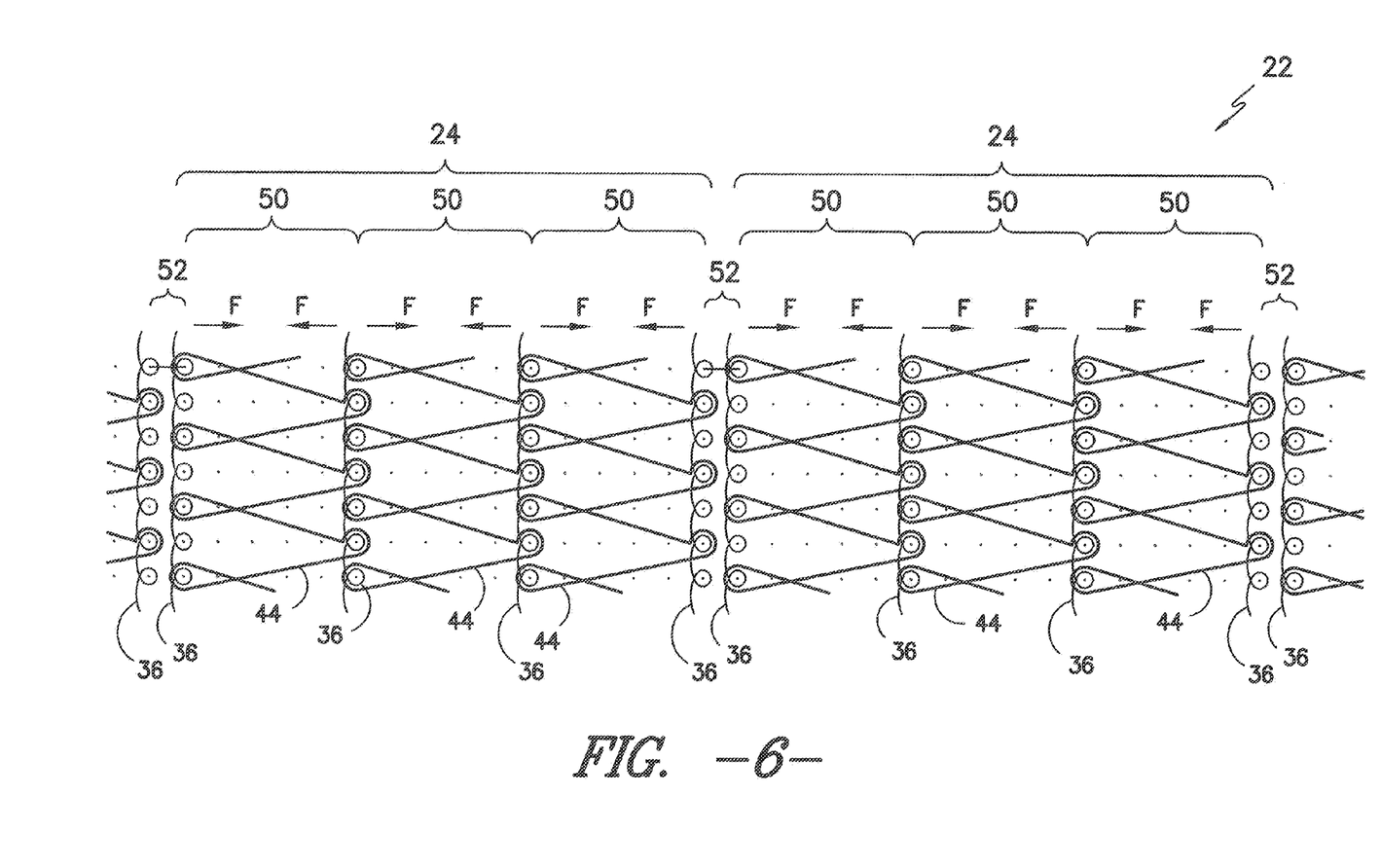
FIG. 6 is a needle point diagram illustrating the elastomeric yarns of FIG. 4 stitched in a switch-back pattern running between border linear stitch lines formed by the inelastic yarns of FIG. 5 to form groups of ladder segments oriented in the machine direction of fabric formation.

Referring now to FIGS. 4-6, in accordance with one exemplary practice for forming the body of the tab member 14, the inelastic yarns 36 of low stretch character may be stitched in a partially threaded pattern with a chain stitch notation as shown in FIG. 5 to form linear stitch lines running in the machine direction of the stretchable fabric 28. As will be appreciated, such linear stitch lines may be formed by having each of the inelastic yarns 36 engage a single needle 34 during the formation process without shifting between needles. In this regard, while a chain stitch notation may be particularly desirable, other stitch notations such as tricot stitches or the like forming substantially linear stitch lines may likewise be used if desired. As best seen through reference to FIG. 6, the linear stitch lines formed by the inelastic yarns 36 define lateral boundaries for individual stitched-in ladder segments 50 which cooperatively form the expansion zone 22 within the stretchable tab member 14.

As best seen through joint reference to FIGS. 4 and 6, in the exemplary configuration the elastomeric yarns 44 are stitched with a notation such that they run in a switch-back pattern between opposing linear stitch lines formed by the inelastic yarns 36. Thus, segments of the elastomeric yarns 44 are arranged substantially in the cross machine direction to form interior portions of the stitched-in ladder segments 50. As will be appreciated, such a switch-back arrangement may be formed by shifting each of the elastic yarns 44 back and forth between the needles which engage the inelastic yarns 36 during the formation process. Of course, the needles which are not engaged may be removed if desired.

As best seen through joint reference to FIGS. 6 and 7, the elastomeric yarns 44 are stitched in a tensioned state such that they exert a continuous biasing force exemplified by the force arrows in FIG. 6. This biasing force acts to draw the boundary edges of the ladder segments 50 inwardly towards one another thereby resulting in the formation of the expansible accordion pleats 26. As shown, in the exemplary construction each of the expansible accordion pleats 26 corresponds to one of the ladder segments 50. Moreover, as best seen in FIG. 7, it has been found that in the exemplary construction, the expansible accordion pleats 26 on each side of the stretchable fabric 28 lean in a common direction away from a central axis 51. As will be appreciated, this common leaning orientation aids in permitting the pleats to assume a relatively low profile across the surface of the final tab member 14.

In practice, the stitch-bonding machine may be threaded with the inelastic yarns 36 and the elastomeric yarns 44 in a pattern to provide a desired number and concentration of expansible accordion pleats 26 in the expansion zone 22 of the tab member 14. In particular, the stitch-bonding machine may be threaded to provide multiple groups of ladder segments 50 to define the sub-zones 24 of pleats within the expansion zone 22. The sub-zones 24 may be spaced apart from one another by relatively narrow intermediate spacing segments 52 of inelastic character which extend along the machine direction. The presence of such spacing segments 52 has been found to aid in maintaining dimensional stability of the tab member 14 transverse to the stretch direction. Specifically, such spacing segments 52 may substantially traverse the width of the tab member 14 from the top edge to the bottom edge and act to substantially prevent expansion and contraction in the width dimension of the tab member during stretch and recovery of the expansion zone 22 in length direction.

According to one exemplary practice, the inelastic yarns 36 and elastomeric yarns 44 may be partially threaded to engage selected needles 34 across the width of the stitch-bonding machine according to a pattern to produce the construction illustrated in FIGS. 6 and 7. Starting from the center and working right in FIG. 7, the exemplary pattern for the inelastic yarns 36 is as follows:
  (i) (1 miss 2)×2 to form a substantially inelastic segment which will become the distal end 18;
  (ii) (2 miss 4), (1 miss 4)×2, (2 miss 4), (1 miss 4)×2, (2 miss 4), (1 miss 4)×2, as shown in FIG. 6 to form an expansion zone 22 with three sub-zones 24 which each have three pleats and with an intermediate spacing segment 52 between each of the sub-zones; and
  (iii) (2 miss 2) to anchor the edge of the expansion zone adjacent the proximal end 16.

The exemplary pattern for the elastomeric yarns 44 is (1 miss 4) across the full width of the expansion zone 22.

As will be appreciated, these exemplary stitch notations correspond to expansible accordion pleats 26 that are each formed by ladder segments 50 having a width corresponding to 5 needle lines (i.e. removing 4 needles) between anchoring stitches. Of course this distance may be increased or decreased as desired. In this regard, increasing the width will result generally in larger pleats while decreasing the width will result generally in smaller pleats. The pleats themselves are free of stitches and may be flattened to permit stretching. The exemplary stitch notations also correspond to intermediate spacing segments 52 having a width generally corresponding to the spacing between needle lines. This width may be increased by skipping one or more needle lines if desired. Thus, the final character of the expansion zone 22 is subject to a wide range of possibilities.

As illustrated in FIG. 7, a minor image threading pattern may be applied on the left-hand side of the stretchable fabric 28. With this configuration, the stretchable fabric 28 may be cut in the cross-machine direction and then bisected along the central axis 51 to produce two substantially identical body portions for tab members 14 having a structure as best seen in FIG. 2. As will be understood, in the exemplary construction, the width dimension of the tab member 14 corresponds generically to the machine direction of the stretchable fabric 28 while the length dimension (i.e. the stretch dimension) of the tab member 14 corresponds generically to the cross-machine direction of the stretchable fabric 28.

Figure 8:
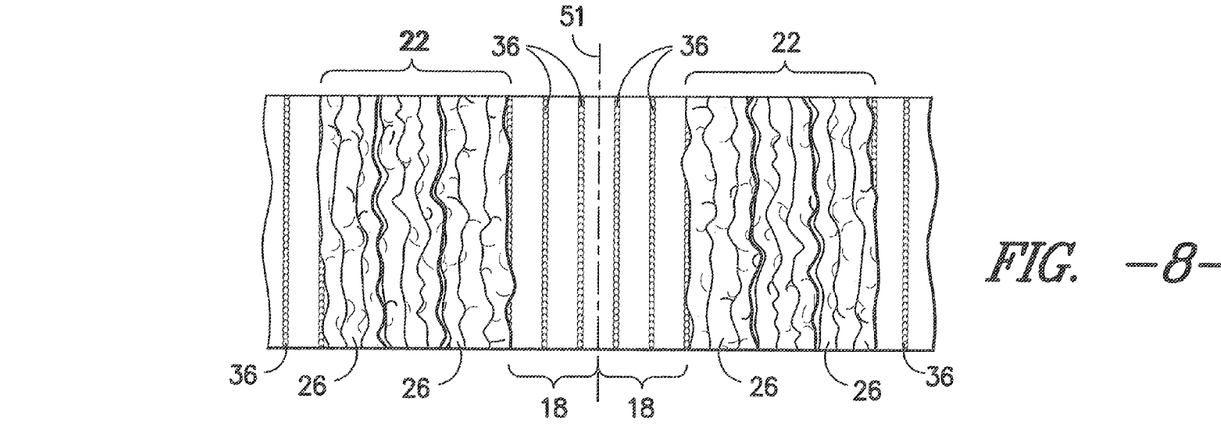
FIG. 8 is a schematic surface view of the exemplary stitch-bonded fabric taken generally along line 8-8 in FIG. 7.

FIG. 8 illustrates the pleated surface of the stretchable fabric 28 which may be bisected to form the body portion of the stretchable tab member 14. In this regard, it should be noted that the expansible accordion pleats 26 are present across the so called "technical face" of the fabric 28 which is the face projecting downward at the needle zone in FIG. 2. Likewise, the underside of the stretchable tab member 14 corresponds to the so called "technical back" of the fabric 28 which is the face projecting upward at the needle zone in FIG. 3.

Figure 9:
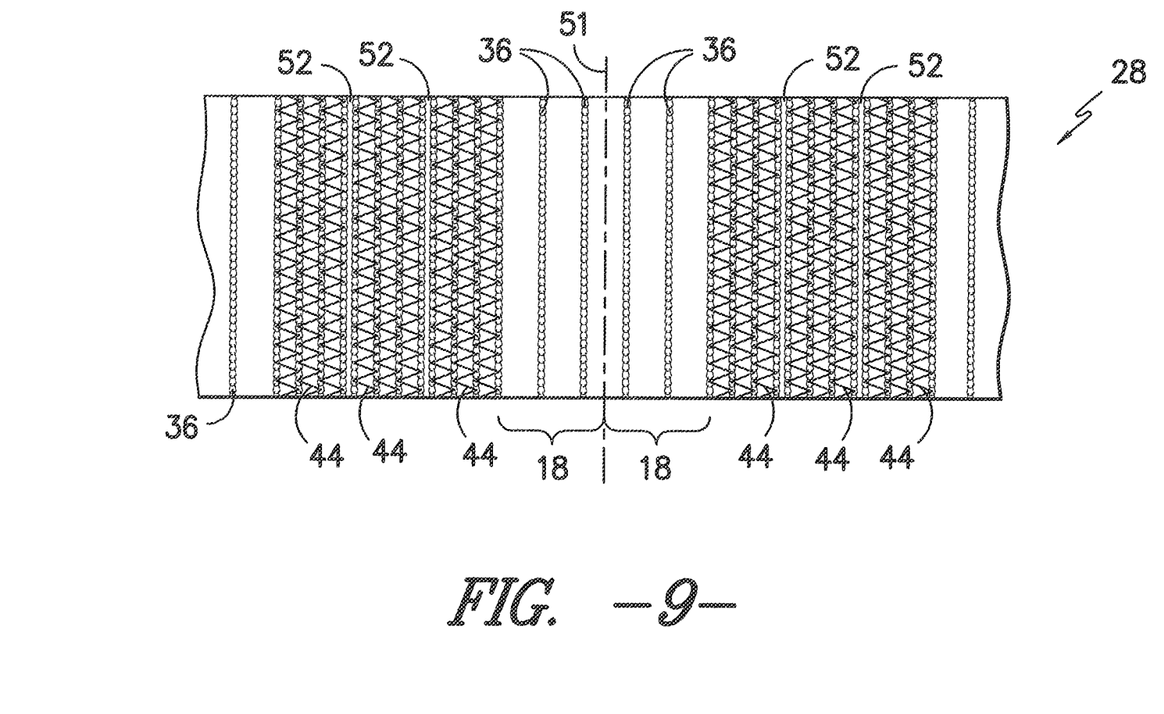
FIG. 9 is a schematic surface view of the exemplary stitch-bonded fabric taken generally along line 9-9 in FIG. 7.

FIG. 9 illustrates the underside of the stretchable fabric 28. As shown, the crossing portions of the elastomeric yarns 44 extending between the linear stitch lines define a zigzag network applying contracting forces to the stitching substrate in the length dimension of the tab member 14 to form the expansible accordion pleats 26. Thus, the zigzag network of elastomeric yarns 44 is disposed in underlying relation to the pleats 26.

In the exemplary embodiment, the substrate material 30 extends continuously from the expansion zone 22 to the distal end 18 to define an attachment surface for the hook fabric 20. As illustrated, one or more linear stitch lines of inelastic yarns 36 may run in the machine direction within the distal end to provide cohesion and dimensional stability. Thus, the distal end may have a substantially inelastic character.

As noted previously, the presence of inelastic spacing segments 52 within the expansion zone 22 aids in preventing substantial expansion and contraction of the tab member 14 in the width dimension during stretch and recovery of the expansion zone 22 in length direction. In particular, with such spacing segments in place and extending between the top edge and the bottom edge of the tab member 14, a 50% extension of the expansion zone 22 in the length dimension is accompanied by less than about 10% reduction in the width dimension. As previously noted, the use of a stitching substrate incorporating a carded thermobond web with a fiber orientation aligned substantially in the machine direction may also aid in stabilizing the width dimension of the tab member 14.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include all alternative embodiments and equivalents to the extent permitted by the prior art.

The invention claimed is:

1. A diaper fastening system comprising:
a landing zone disposed across a portion of the diaper adapted for positioning in overlying relating to a wearer's abdomen, the landing zone having a surface at least partially covered with a material defining a first half of a hook and loop connection system; and
at least one elastomeric connection tab disposed at a side portion of the diaper, the connection tab having a body portion of stitch-bonded construction including a free end projecting away from the diaper, the free end having a base operatively connected to a material forming a second half of the hook and loop connection system, wherein the body portion includes an elastomeric expansion zone, the elastomeric expansion zone including an inelastic stitching substrate comprising one or more layers of fibrous material, wherein the elastomeric expansion zone includes a plurality of accordion pleats of the stitching substrate with a zigzag network of elastomeric yarns disposed in underlying relation to the pleats, wherein the zigzag network is adapted to apply contracting forces to the stitching substrate in the length dimension of the connection tab, wherein one or more members of said plurality of accordion pleats are formed by corresponding stitched-in ladder segments including an elastomeric yarn stitched in tension through the stitching substrate in switch-back relation between opposing linear stitch lines of inelastic yarns stitched through the stitching substrate, wherein the linear stitch lines are oriented transverse to the direction of stretch and wherein the elastomeric expansion zone is reversibly stretchable in the length dimension of the connection tab to at least 150% of its initial length without failure.

2. The diaper fastening system as recited in claim 1, comprising a pair of elastomeric connection tabs disposed on opposing sides of the diaper.

3. The diaper fastening system as recited in claim 1, wherein a loop fabric is disposed at the landing zone and a hook fabric is disposed at the free end.

4. The diaper fastening system as recited in claim 1, wherein two or more members of said plurality of accordion pleats are formed by adjacent stitched-in ladder segments arranged in side-by-side contacting relation with the adjacent stitched-in ladder segments sharing a common linear stitch line at the intersection between the adjacent stitched-in ladder segments.

5. The diaper fastening system as recited in claim 1, wherein the elastomeric expansion zone includes a first group of accordion pleats and at least a second group of accordion pleats separated by an inelastic spacing segment.

6. The diaper fastening system as recited in claim 5, wherein accordion pleats within each of the first group and the second group are formed by adjacent stitched-in ladder segments arranged in side-by-side contacting relation with the adjacent stitched-in ladder segments sharing a common linear stitch line at the intersection between the adjacent stitched-in ladder segments.

7. The diaper fastening system as recited in claim 1, wherein the stitching substrate comprises multiple plies of non-woven fibrous material oriented in layered relation and wherein the total mass per unit area of the stitching substrate is in the range of about 15 to 150 grams per square meter.

8. The diaper fastening system as recited in claim 7, wherein one or more of the plies of non-woven fibrous material is a spun bonded polypropylene fleece having a mass per unit area of about 5 to 50 grams per square meter.

9. The diaper fastening system as recited in claim 7, wherein one or more of the plies of non-woven fibrous material is a carded thermobond web of polypropylene fiber having a mass per unit area of about 10 to 80 grams per square meter with fibers oriented predominantly in the width dimension of the connection tab.

10. The diaper fastening system as recited in claim 7, wherein the stitching substrate comprises multiple plies of carded thermobond polypropylene fiber web material in layered relation with one or more plies of spun bonded polypropylene fleece, and wherein fibers within the thermobond polypropylene fiber web material are oriented predominantly in the width dimension of the connection tab.

11. A diaper fastening system comprising:
a landing zone disposed across a portion of the diaper adapted for positioning in overlying relating to a wearer's abdomen, the landing zone having a surface at least partially covered with a material defining a first half of a hook and loop connection system; and
at least one elastomeric connection tab disposed at a side portion of the diaper, the connection tab having a body portion of stitch-bonded construction including a free end projecting away from the diaper, the free end having a base operatively connected to a material forming a second half of the hook and loop connection system, wherein the body portion includes an elastomeric expansion zone disposed rearward from the free end, the elastomeric expansion zone including an inelastic stitching substrate comprising one or more layers of fibrous material, wherein the elastomeric expansion zone includes a plurality of accordion pleats of the stitching substrate with a zigzag network of elastomeric yarns disposed in underlying relation to the pleats, wherein the zigzag network is adapted to apply contracting forces to the stitching substrate in the length dimension of the connection tab, wherein one or more members of said plurality of accordion pleats are formed by corresponding stitched-in ladder segments including an elastomeric yarn stitched in tension through the stitching substrate in switch-back relation between opposing linear stitch lines of inelastic yarns stitched through the stitching substrate, wherein the linear stitch lines are oriented transverse to the direction of stretch and wherein a portion of the stitching substrate extends away from the expansion zone and defines the base operatively connected to the material forming the second half of the hook and loop connection, and wherein the elastomeric expansion zone includes a first group of accordion pleats and at least a second group of accordion pleats separated by an inelastic spacing segment which extends in substantially spanning relation across the entire width of the elastomeric connection tab, and wherein the elastomeric expansion zone is stretchable in the length dimension of the connection tab to at least 150% of its initial length without failure.

12. The diaper fastening system as recited in claim 11, comprising a pair of elastomeric connection tabs disposed on opposing sides of the diaper.

13. The diaper fastening system as recited in claim 11, wherein a loop fabric is disposed at the landing zone and a hook fabric is disposed at the free end of the connection tab.

14. The diaper fastening system as recited in claim 11, wherein two or more members of said plurality of accordion pleats are formed by adjacent stitched-in ladder segments arranged in side-by-side contacting relation with the adjacent stitched-in ladder segments sharing a common linear stitch line at the intersection between the adjacent stitched-in ladder segments.

15. The diaper fastening system as recited in claim 11, wherein accordion pleats within each of the first group and the second group are formed by adjacent stitched-in ladder segments arranged in side-by-side contacting relation with the adjacent stitched-in ladder segments sharing a common linear stitch line at the intersection between the adjacent stitched-in ladder segments.

16. The diaper fastening system as recited in claim 11, wherein the stitching substrate comprises multiple plies of non-woven fibrous material oriented in layered relation and wherein the total mass per unit area of the stitching substrate is in the range of about 15 to 150 grams per square meter.

17. The diaper fastening system as recited in claim 16, wherein one or more of the plies of non-woven fibrous material is a spun bonded polypropylene fleece having a mass per unit area of about 5 to 50 grams per square meter.

18. The diaper fastening system as recited in claim 16, wherein one or more of the plies of non-woven fibrous material is a carded thermobond web of polypropylene fiber having a mass per unit area of about 10 to 80 grams per square meter with fibers oriented predominantly in the width dimension of the connection tab.

19. The diaper fastening system as recited in claim 16, wherein the stitching substrate comprises multiple plies of carded thermobond polypropylene fiber web material in layered relation with one or more plies of spun bonded polypropylene fleece, and wherein fibers within the thermobond polypropylene fiber web material are oriented predominantly in the width dimension of the connection tab.

20. A diaper fastening system comprising:
a landing zone disposed across a portion of the diaper adapted for positioning in overlying relating to a wearer's abdomen, the landing zone having a surface at least partially covered with a material defining a first half of a hook and loop connection system; and
at least one elastomeric connection tab disposed at a side portion of the diaper, the connection tab having a unitary body portion of stitch-bonded construction including a free end projecting away from the diaper, the free end having a base operatively connected to a material forming a second half of the hook and loop connection system, wherein the body portion includes an elastomeric expansion zone disposed rearward from the free end, the elastomeric expansion zone including an inelastic stitching substrate comprising one or more layers of fibrous material, wherein the elastomeric expansion zone includes a plurality of accordion pleats of the stitching substrate with a zigzag network of elastomeric yarns disposed in underlying relation to the pleats, wherein the zigzag network is adapted to apply contracting forces to the stitching substrate in the length dimension of the connection tab, wherein one or more members of said plurality of accordion pleats are formed by corresponding stitched-in ladder segments including an elastomeric yarn stitched in tension through the stitching substrate in switch-back relation between opposing linear stitch lines of inelastic yarns stitched through the stitching substrate, wherein the linear stitch lines are oriented transverse to the direction of stretch and wherein a portion of the stitching substrate extends away from the expansion zone and defines the base operatively connected to the material forming the second half of the hook and loop connection, wherein at least a first one of said ladder segments is oriented in side-by-side contacting relation with at least a second one of said ladder segments to define a contiguous group of ladder segments disposed across a portion of the expansion zone and wherein a common linear stitch line is shared by adjacent ladder segments within the contiguous group, and wherein two or more of said contiguous groups are disposed in spaced-apart relation within the elastomeric expansion zone with inelastic spacing segments of the stitching substrate disposed between adjacent contiguous groups, wherein the inelastic spacing segments extend substantially between upper lower edges of the elastomeric connection tab, wherein the elastomeric expansion zone is stretchable in the length dimension of the connection tab from the untensioned condition to at least 150% of its initial length without failure, with subsequent recovery to within 15% of its initial length upon removal of tensioning force, and wherein a 50% extension of the expansion zone in the length dimension of the connection tab is accompanied by not more than about a 20% reduction in the width dimension of the connection tab transverse to the direction of stretch.

\* \* \* \* \*